US00PP19505P2

(12) United States Plant Patent
van der Helm

(10) Patent No.: US PP19,505 P2
(45) Date of Patent: Nov. 25, 2008

(54) CARNATION PLANT NAMED 'LUXOR'

(50) Latin Name: *Dianthus caryophyllus*
Varietal Denomination: Luxor

(75) Inventor: Franciscus Jacobus Joseph van der Helm, Aalsmeer (NL)

(73) Assignee: Kooij + Zonen B.V., Aalsmeer (NL)

( * ) Notice: Subject to any disclaimer, the term of this patent is extended or adjusted under 35 U.S.C. 154(b) by 92 days.

(21) Appl. No.: 11/483,249

(22) Filed: Jul. 7, 2006

(51) Int. Cl.
*A01H 5/00* (2006.01)

(52) U.S. Cl. ..... Plt./278

(58) Field of Classification Search ..... Plt./278
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of Carnation plant named 'Luxor', characterized by its compact, upright, somewhat outwardly spreading and mounded plant habit; moderately vigorous growth habit; freely branching habit; numerous light red-colored fragrant flowers that are positioned above and beyond the foliage; and good flower longevity.

1 Drawing Sheet

Botanical designation: *Dianthus caryophyllus.*
Cultivar denomination: 'Luxor'.

BACKGROUND OF THE INVENTION

The present invention relates to a new and distinct cultivar of Carnation plant, botanically known as *Dianthus caryophyllus,* grown as a potted plant, and hereinafter referred to by the name 'Luxor'.

The new Carnation is a product of a planned breeding program conducted by the Inventor in Aalsmeer, The Netherlands. The objective of the breeding program was to develop new freely-branching Carnation cultivars with numerous flowers and attractive flower coloration.

The new Carnation originated from a cross-pollination made by the Inventor in May, 2001, of a proprietary selection of *Dianthus caryophyllus* identified as code number 996108-01, not patented, as the female, or seed, parent with a proprietary selection of *Dianthus caryophyllus* identified as code number 996078-01, not patented, as the male, or pollen, parent. The cultivar Luxor was discovered and selected by the Inventor as a flowering plant within the progeny of the stated cross-pollination in a controlled environment in Aalsmeer, The Netherlands in July, 2002.

Asexual reproduction of the new cultivar by terminal cuttings propagated in a controlled environment in Aalsmeer, The Netherlands since 2002, has shown that the unique features of this new Carnation are stable and reproduced true to type in successive generations of asexual reproduction.

SUMMARY OF THE INVENTION

The cultivar Luxor has not been observed under all possible environmental conditions. The phenotype may vary somewhat with variations in environment such as temperature and light intensity, without, however, any variance in genotype.

The following traits have been repeatedly observed and are determined to be the unique characteristics of 'Luxor'. These characteristics in combination distinguish 'Luxor' as a new and distinct cultivar of Carnation:

1. Compact, upright, somewhat outwardly spreading and mounded plant habit.
2. Moderately vigorous growth habit.
3. Freely branching habit.
4. Numerous light red-colored fragrant flowers that are positioned above and beyond the foliage.
5. Good flower longevity.

In side-by-side comparisons conducted in Aalsmeer, The Netherlands, plants of the new Carnation differ from plants of the light red-colored parent selections in the following characteristics:

1. Plants of the new Carnation are more compact than plants of the parent selections.
2. Plants of the new Carnation have smaller flowers than plants of the parent selections.
3. Plants of the new Carnation have entire petals whereas plants of the parent selections have serrate petals.

Plants of the new Carnation can be compared to plants of the Carnation cultivar Pink Surprise, disclosed in U.S. Plant Pat. No. 13,308. In side-by-side comparisons conducted in Aalsmeer, The Netherlands, plants of the new Carnation differed from plants of the cultivar Pink Surprise in the following characteristics:

1. Plants of the new Carnation were larger than plants of the cultivar Pink Surprise.
2. Plants of the new Carnation had larger flowers than plants of the cultivar Pink Surprise.
3. Plants of the new Carnation had entire petals whereas plants of the cultivar Pink Surprise had serrated petals.

BRIEF DESCRIPTION OF THE PHOTOGRAPH

The accompanying photograph illustrates the overall appearance of the new Carnation. This photograph shows the colors as true as it is reasonably possible to obtain in colored reproductions of this type. Colors in the photograph may differ slightly from the color values cited in the detailed botanical description which accurately describe the colors of the new Carnation. The photograph comprises a side perspective view of a typical flowering plant of 'Luxor' grown in a container.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Aalsmeer, The Netherlands during the summer in a glass-covered greenhouse and under conditions and practices which approximate those generally used in commercial potted Carnation production. During the production of the plants, day temperatures averaged 20° C. and night temperatures averaged 12° C. Measurements and numerical values represent averages for typical flowering plants. Single plants were grown in 10-cm pots and were pinched one time. Plants were about four months old when the photographs and the detailed description were taken.

Botanical classification: *Dianthus caryophyllus* cultivar Luxor.

Parentage:

*Female, or seed, parent.*—Proprietary selection of *Dianthus caryophyllus* identified as code number 996108-01, not patented.

*Male, or pollen, parent.*—Proprietary selection of *Dianthus caryophyllus* identified as code number 996078-01, not patented.

Propagation:

*Type.*—Terminal cuttings.

*Time to initiate roots, summer.*—About one week at 25° C.

*Time to initiate roots, winter.*—About ten days at 20° C.

*Time to produce a rooted young plant, summer.*—About three weeks at 25° C.

*Time to produce a rooted young plant, winter.*—About four weeks at 20° C.

*Root description.*—Fine, fibrous; white in color.

*Rooting habit.*—Freely branching.

Plant description:

*Plant form.*—Compact, upright, somewhat outwardly spreading and mounded plant habit; inverted triangle.

*Growth and branching habit.*—Moderately vigorous and freely-branching growth habit with about five primary lateral branches; dense and bushy growth habit. Pinching, that is removal of the terminal apex, enhances lateral branching.

*Plant height.*—About 18 cm.

*Plant diameter or spread.*—About 15 cm.

*Lateral branches.*—Length: About 6 cm. Diameter: About 3 mm. Internode length: About 1.5 cm. Texture: Smooth, glabrous. Color: 138C.

Foliage description:

*Arrangement.*—Opposite, simple; sessile.

*Length.*—About 5 cm.

*Width.*—About 5 mm.

*Shape.*—Linear.

*Apex.*—Acute.

*Base.*—Truncate.

*Margin.*—Entire.

*Texture, upper and lower surfaces.*—Smooth, glabrous; glaucous.

*Venation pattern.*—Pinnate.

*Color.*—Developing foliage, upper surface: 137B. Developing foliage, lower surface: 137C. Fully expanded foliage, upper surface: 137A; venation, 137A. Fully expanded foliage, lower surface: 137B; venation, 137B.

Flower description:

*Flower type and habit.*—Semi-double flowers. Freely flowering habit; usually four open flowers per lateral branch. Flowers positioned above and beyond the foliage; typically facing upright. Flowers persistent. Flowers strongly fragrant; clove-like.

*Natural flowering season.*—Flowering is continuous through the summer in The Netherlands. Flowers last about two weeks on the plant.

*Flower diameter.*—About 4.5 cm.

*Flower depth.*—About 2 cm.

*Flower buds.*—Length: About 2 cm. Diameter: About 8 mm. Shape: Obovate. Color: 137D.

*Petals/petaloids.*—Quantity/arrangement: About 18 per flower in several whorls. Length, outer petals: About 4 cm. Width, outer petals: About 1.5 cm. Shape: Roughly spatulate. Apex: Rounded. Base: Acute. Margin: Entire. Texture, upper and lower surfaces: Smooth, glabrous. Color: When opening and fully opened, upper surface: 47C; color becoming closer to 48C with development. When opening and fully opened, lower surface: 48C.

*Sepals.*—Quantity/arrangement: Five fused in a single whorl. Length: About 5 mm. Width: About 2 mm. Shape: Narrowly triangular. Apex: Acute. Margin: Entire. Texture, upper and lower surfaces: Smooth, glabrous. Color, upper and lower surfaces: 137C.

*Peduncles.*—Length: About 5 mm. Diameter: About 1 mm. Strength: Moderately strong. Texture: Smooth, glabrous. Color: 137C.

*Reproductive organs.*—Stamens: Quantity: Five per flower. Anther length: About 2 mm. Anther shape: Oblong. Pollen amount: Moderate. Pistils: Quantity: Two per flower. Pistil length: About 3 cm. Stigma shape: Curled. Stigma color: 155A. Style length: About 1 cm. Style color: 155A. Ovary color: 145B.

*Fruits.*—Type: Capsule. Time to ripening: About six weeks. Length: About 1 cm. Diameter: About 7 mm. Texture: Smooth, glabrous. Color: 137B.

*Seeds.*—Quantity: Five per capsule. Length: About 2 mm. Diameter: About 1 mm. Color: 202A.

Disease/pest resistance: Plants of the new Carnation have not been observed to be resistant to pathogens and pests common to Carnations.

Temperature tolerance: Plants of the new Carnation have been observed to tolerate temperatures ranging from −5° C. to 40° C.

It is claimed:

1. A new and distinct Carnation plant named 'Luxor' as illustrated and described.

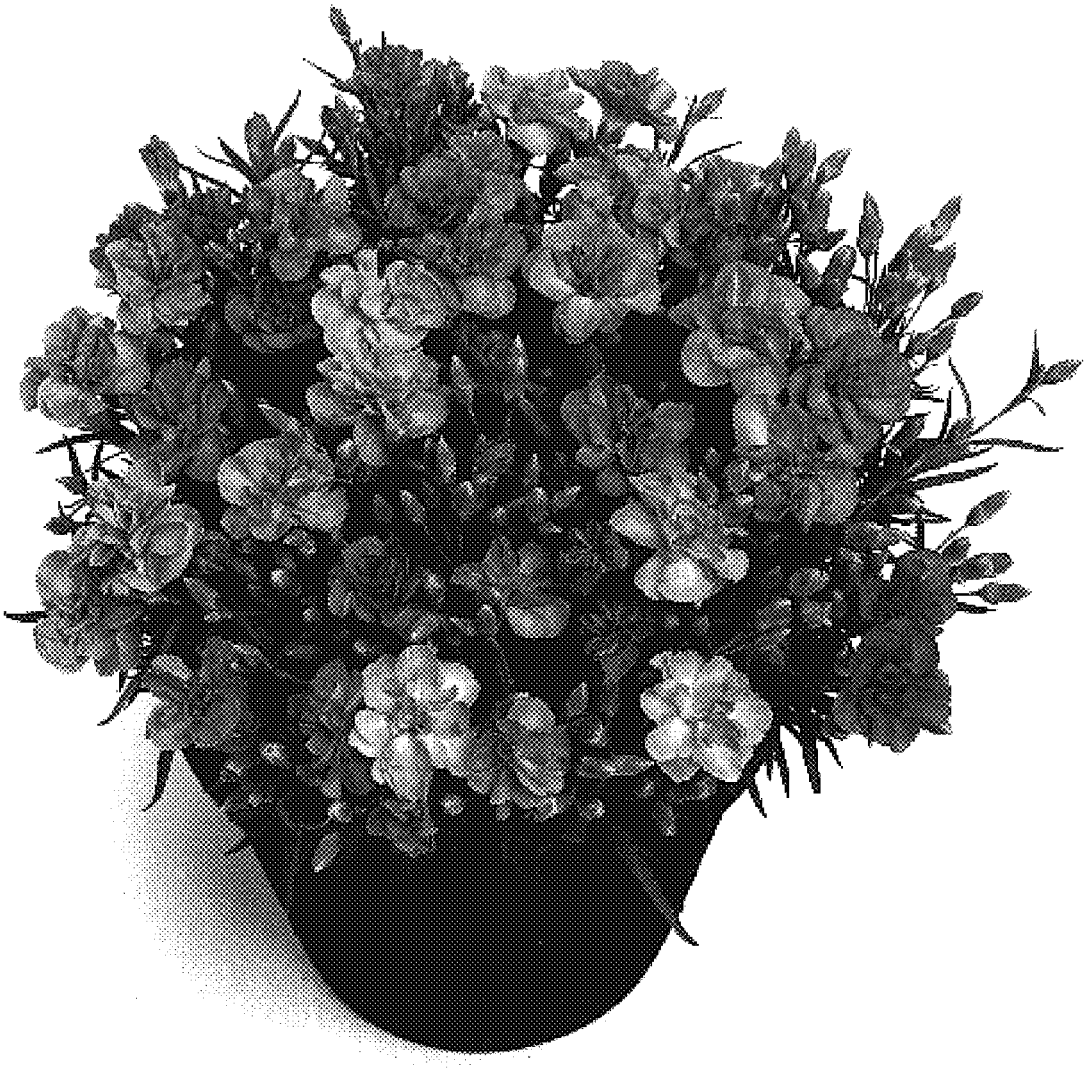

* * * * *